(12) United States Patent
Thomas

(10) Patent No.: US 6,582,798 B2
(45) Date of Patent: Jun. 24, 2003

(54) VACUUM FORMED FILM TOPSHEETS HAVING A SILKY TACTILE IMPRESSION

(75) Inventor: Paul E. Thomas, Terre Haute, IN (US)

(73) Assignee: Tredegar Film Products Corporation, Richmond, VA (US)

( * ) Notice: Subject to any disclaimer, the term of this patent is extended or adjusted under 35 U.S.C. 154(b) by 62 days.

(21) Appl. No.: 09/876,440

(22) Filed: Jun. 6, 2001

(65) Prior Publication Data

US 2003/0059574 A1 Mar. 27, 2003

(51) Int. Cl.⁷ .................... B32B 3/24; A61F 13/512; A61F 13/511
(52) U.S. Cl. .................. 428/132; 428/137; 428/131; 428/138; 428/141; 428/167; 428/220; 428/913; 604/378; 604/383
(58) Field of Search .................. 428/132, 137, 428/131, 138, 167, 141, 220, 913; 604/378, 383

(56) References Cited

U.S. PATENT DOCUMENTS

| | | | |
|---|---|---|---|
| 2,304,632 A | * 12/1942 | Faelten ................ 106/171.1 |
| 3,929,135 A | 12/1975 | Thompson ................ 128/287 |
| 4,151,240 A | 4/1979 | Lucas et al. ............... 264/504 |
| 4,252,516 A | 2/1981 | Raley et al. ............... 425/290 |
| 4,327,730 A | 5/1982 | Sorenson ................ 128/287 |
| 4,342,314 A | 8/1982 | Radel et al. ............... 128/287 |
| 4,456,570 A | 6/1984 | Thomas et al. ............ 264/22 |
| 4,463,045 A | 7/1984 | Ahr et al. ................ 428/131 |
| 4,508,256 A | 4/1985 | Radel et al. ............... 228/152 |
| 4,629,643 A | 12/1986 | Curro et al. ............... 428/131 |
| 4,655,759 A | 4/1987 | Romans-Hess et al. . 604/385 R |
| 4,758,240 A | 7/1988 | Glassman ................ 604/379 |
| 4,839,216 A | 6/1989 | Curro et al. ............... 428/134 |
| 4,859,519 A | 8/1989 | Cabe, Jr. et al. ............ 428/131 |
| 4,995,930 A | 2/1991 | Merz et al. ................ 156/209 |
| 5,078,710 A | * 1/1992 | Suda et al. ................ 428/137 |
| 5,268,213 A | 12/1993 | Murakami et al. .......... 428/163 |
| 5,427,838 A | 6/1995 | Yamamoto et al. ......... 428/167 |
| 5,514,105 A | 5/1996 | Goodman, Jr. et al. ..... 604/370 |
| H1575 H | 8/1996 | Daugherty et al. ......... 428/284 |
| 5,591,510 A | * 1/1997 | Junker et al. ............... 428/131 |
| 5,648,142 A | 7/1997 | Phillips ................ 428/132 |
| 5,728,446 A | 3/1998 | Johnston et al. ............ 428/167 |
| 5,731,061 A | 3/1998 | Bezier ................ 428/131 |
| 6,090,089 A | * 7/2000 | Tsuji et al. ................ 156/219 |
| 6,242,074 B1 | 6/2001 | Thomas ................ 428/137 |
| 6,452,063 B1 | * 9/2002 | Curro et al. ................ 428/131 |

FOREIGN PATENT DOCUMENTS

| | | |
|---|---|---|
| DE | 4437165 | 4/1996 |
| DE | 19846857 | 3/2000 |
| EP | 0 858 792 A2 | 8/1998 |
| EP | 0 995 414 A1 | 4/2000 |
| WO | WO 99/62449 | 12/1999 |

OTHER PUBLICATIONS

Search Report, RS 107330 US; Mailed Dec. 21, 2001.

* cited by examiner

Primary Examiner—William P. Watkins, III
(74) Attorney, Agent, or Firm—Jenkens & Gilchrist, P.C.

(57) ABSTRACT

A vacuum formed film that delivers desirable rewet properties and possesses a desirable silky tactile impression or silky feel to a user. The vacuum formed film may have a plurality of cells, wherein the cells are ellipse shaped, each having a major axis and minor axis. The cells may also be boat shaped, wherein the ends of the cell on each end of the major axis are rounded off. The cells may also be oval shaped. Major axes of the cells are aligned in the stroking direction of the vacuum formed film. The cells define stroking direction lands and transverse direction lands in areas between the cells. The stroking direction lands may also be raised with respect to the transverse direction lands. Micro-ridges may be formed on the lands for imparting a silky feel to the vacuum formed film. The various film aspects, above, each contribute to the silky tactile impression of the film. Some or all of the various aspects described above may be combined to achieve a further improved silky tactile impression.

9 Claims, 6 Drawing Sheets

VACUUM FORMED FILM TOPSHEETS HAVING A SILKY TACTILE IMPRESSION

FIELD OF THE INVENTION

The present invention relates to disposable absorbent products. More particularly, the present invention relates to an apertured, vacuum formed film having properties that give the film a silky tactile impression or silky feel when the film is stroked by a user.

BACKGROUND OF THE INVENTION

Advances in film forming technology have yielded improvements in disposable absorbent products such as disposable diapers, feminine hygiene products and the like. "Film" is a common term for thermoplastic polymer webs made from any variety of processes. The most common method of producing films is with an extrusion process.

Cast extrusion and blown extrusion are commonly known methods in the film producing industry. In a blown extrusion process, a circular die extrudes an inflated bubble of film that is cooled by cool air streams blown onto the bubble's perimeter by an air ring. The bubble is then flattened in a nip and subsequently slit into flat sheets that can then be reheat embossed or otherwise manipulated. Blown film can be used to create a roll of precursor film that may be fed into a reheat vacuum formed film (VFF) process. This method is taught by U.S. Pat. No. 4,151,240 to Lucas. Additionally, it is also known to use a precursor roll of cast film.

In a cast extrusion process, a flat web is extruded from a slot die. The flat web is subsequently cooled and set by a variety of chilling roller means. As an example, U.S. Pat. No. 4,456,570 to Thomas teaches a cast extrusion in a direct melt vacuum formed film (VFF) process. In a vacuum formed film process, a pressure differential is applied across a forming screen. In the case of a direct melt VFF process, a molten web is extruded onto a forming area of a forming screen. An example of a direct melt VFF process is taught by U.S. Pat. No. 4,456,570 to Thomas. U.S. Pat. No. 4,151,240 to Lucas teaches reheating and partially melting a web while the web is over the forming area of the forming screen. A melted polymer is desirable to form three-dimensional apertures since a melted polymer is more easily sucked into the apertures in a forming screen. Both U.S. Pat. No. 4,456,570 to Thomas and U.S. Pat. No. 4,151,240 to Lucas teach primarily using vacuum as a main source of pressure differential energy that is used for the work energy that changes a two dimensional web into a three dimensional cell and causes an aperture to open in a film web. During the formation of a VFF, the polymer of the film typically undergoes a phase change from molten state in a flat form to a crystalline state in the new three dimensional form.

In some cases, it is desirable to form textures on the lands of the VFF. To form textures on the lands of the vacuum formed film, lands are provided on the forming screen with textures provided thereon. The textures on the forming screen are then incorporated into the direct melt VFF film. Due to vacuum pressure, textures form on the lands of the subsequently formed VFF. As discussed above, the vacuum pressure differential also causes 3-D cells with apertures to be formed in the film.

The textures imparted on the VFF may be formed in a pattern. Examples of embossing patterns include straight lines, pyramids, diamonds, squares, and random matte. Further, more exotic patterns may be used including, exotic squiggly lines, spiral pattens, microscopic flower petals, and other ornamental designs.

A micropattern can also be incorporated into a precursor film by a reheat VFF process, via either cast embossing or blown embossing processes that are well known in the industry and that are discussed above. In a reheat process, external heat is applied to partially melt and form three dimensional cells with apertures. Portions of the precursor film rest on the lands of the screen, which partially protects these portions of the precursor film from the heat. Therefore, only the portion of the film suspended over an opening of a cell in the forming screen is fully unprotected from exposure to heat. Thus, the suspended portion becomes melted and forms a three dimensional cell with an aperture.

When a film layer is applied to a forming screen, the film layer typically has about 25 to 80 times less mass than a metallic screen mass beneath the film layer. Because of the mass ratio of the film layer to the screen, the screen acts as a "heat sink" in the land area where the precursor film is in intimate contact with the lands of the forming screen. The heat passes through the thin film and is absorbed by the screen such that no, or negligible, thermal distortion occurs on the land regions. As a result, any texturizing pattern embossed into the precursor film is maintained in the finished VFF.

Films produced by the methods above may be constructed of various materials having a selected mesh count, embossed thickness, a selected aperture pattern, a selected width of the lands or spaces between the apertures, and a selected pattern may be formed on the lands. The "mesh count" is the number of cells aligned in one inch of distance. Other variations may also be possible. Each configuration will exhibit distinct properties with respect to performance.

When measuring a VFF for percent open area, it is common to use any of the many computerized video devices that are available. The video camera, via magnification and contrast, can discern the openings from the lands and digitize the data to calculate the percent open area.

Unlike nonwoven material (NW), which exhibits capillary action for wicking fluids, formed films are made from polymer webs that do not transmit fluid unless the formed film is "formed" into a three-dimensional apertured sheet. Formed films may be tested for rewet. A lower rewet value is more desirable. Generally, preferred products have had a rewet value of less than one gram; i.e. a "fractional gram". It has been found that products with a gram or more of rewet are typically viewed by consumers as being wet or damp in use.

Fluid acquisition rate is also critical to a functional topsheet. If the fluid acquisition rate is too slow, then a product using the topsheet may leak. The fluid acquisition rate is affected by several factors. The surface energy of the vacuum formed film is critical for fluid acquisition rate. Additionally, the fluid acquisition rate is directly correlated to open area. Additionally, the "loft", or the required spacial distance between a fluid containing absorbent core and the skin of the user, must also have a certain measure to prevent a wetness factor of one gram or greater as exhibited by rewet values. Simply stated, if there are relatively large openings, as indicated by high % open area, and comparatively little separation space, as indicated by low loft, then fluid can overcome the short expanse of space through the center of the large opening, which results in reverse flow, or "rewet".

Table 1, below, is derived from selected feminine napkin products from around the world that use a formed film coversheet. From the data in Table 1, the ratio correlation can be seen. From such data, the apparent line of separation of the loft to % open area ratio (L/OA Ratio) between a "dry"

coversheet and "damp" coversheet would logically be about a L/OA Ratio of ≧10.

TABLE 1

| Product | Loft, μ | Open Area, % | L/OA Ratio | Rewet, grams |
|---|---|---|---|---|
| Always | 550 | 32.0 | 17.0 | 0.05 |
| Equate | 455 | 28.5 | 16.0 | 0.15 |
| Siernpre Libre | 450 | 20.0 | 22.0 | 0.12 |
| Itimus | 370 | 20.0 | 18.5 | 0.10 |
| CareFree (Euro) | 130 | 25.0 | 5.2 | 4.85 |
| Magix | 100 | 21.5 | 4.5 | 6.15 |
| Centre Libre | 190 | 25.0 | 7.6 | 1.90 |

The term "rewet" implies that all of the fluid passes through the topsheet and then only the fluid coming back to the surface to "rewet" it is measured. However, with the many varieties of micro-embossing, crimping, and punching involved with these materials, often "wells" can be formed that trap fluid on the surface. The entrapped fluid accounts for about 15% of variation in the data. Also, as with any reliable test method, the method itself will have some variation of results, even within a given single material. This is offered to explain why the correlation is not exactly linear as, in theory, it should be.

Hole diameter is determined by the narrowest width of an aperture (specifically for aperturing oval or elliptical shapes) that can be determined as a function of mesh count and land width. From mesh count and land width, one can derive an approximate hole diameter, or span of the "supports" for the polymer sheet to be apertured.

A hole diameter of a typically known 60 mesh forming screen is usually no more than 200μ. Since a reasonable amount of metal must remain between holes in a forming screen (such that it will be robust enough to run in the VFF process), one can calculate hole diameter as follows. As explained above, "mesh" is the number of cells aligned in one inch of distance; hence, 1/60=0.017 inch center to center, or 430μ. One will need about 230μ of metal land area to have a robust screen, leaving the nominal 200μ hole diameter for a 60 mesh pattern.

In addition to rewet performance and fluid acquisition performance during use, it has been found that the feel or tactile impression of a topsheet is important to consumers. Silk has been known for centuries to impart a unique and highly desirable tactile impression that has no other description than to say, "This feels silky". The term "silky" alone provides enough description for average global consumers to grasp its meaning and recognize whether or not a product feels "silky" or merely soft and clothlike. In repeated blind panel tests various fabrics such as felt, flannel, cotton diapers, polyester/cotton clothing fabric, wool, and silk were tested. The panels easily discern a silky tactile impression (STI) of silk cloth over the other cloth materials.

For many years, the feminine napkin market has been segmented into women who prefer a nonwoven coversheet and women who prefer a film coversheet. The market segmentation is particularly found in westernized countries. Those who prefer the nonwoven type seem to prefer the clothlike tactile impression and the perceived "comfort" that they derive from it.

Users of the nonwoven type, however, sacrifice the dry cleanliness of the VFF type. Nonwovens have capillarity due to having their many fibers in close proximity to the absorbent core. Capillarity is good for transmitting fluid through a coversheet via the capillary action of the nonwoven. Unfortunately, "wicking" by capillary action can also act in reverse. Therefore, nonwovens are not known for providing good rewet values. A good rewet value is indicative of dry cleanliness during use.

Those who prefer the film type seem to prefer the improved cleanliness and anti-rewet, particularly that of the VFFs. Many VFF coversheets have large openings which readily accept semi-coagulated matter found in menses. VFFs also provide the afore-mentioned prevention of the fluid rewetting to the top plane of the film. The prevention of rewet is derived from the superior loft of the VFF material. Hence, those who prefer the prior art film type forgo a bit of clothlike tactile impression derived from the presence of fibers of a nonwoven to achieve the cleanliness, which is especially true of a VFF. A film that delivers the perceived comfort of a nonwoven with the improved cleanliness and anti-rewet is desirable. Therefore, much effort has been made in attempts to derive the benefits of both types, some with market success; however, no VFF to date has delivered both the cleanliness and a silky tactile impression.

SUMMARY OF THE INVENTION

The present invention relates to a vacuum formed film that delivers desirable rewet properties and possesses a desirable silky tactile impression or silky feel to a user. In one embodiment, the vacuum formed film has a plurality of cells, wherein the cells are ellipse shaped, each having a major axis and minor axis. In another embodiment, the cells are boat shaped, wherein the ends on each end of the major axis are rounded off. In another embodiment the cells may be oval shaped. Major axes of the cells are aligned in the stroking direction of the vacuum formed film. The cells define stroking direction lands and a transverse direction lands in areas between the cells. In one embodiment, the stroking direction lands are raised with respect to said transverse direction lands. In yet another embodiment, micro-ridges are formed on the lands for imparting a silky feel to the vacuum formed film. The various film aspects, above, each contribute to the silky tactile impression of the film. In still further embodiments, some or all of the various aspects described above may be combined to achieve a further improved silky tactile impression. The loft to open area ratio of the vacuum formed film is preferably greater than about 9 and preferably has a rewet of less than about 1 gram.

DETAILED DESCRIPTION OF THE INVENTION

Both direct melt and reheat processes are, in this invention, considered to be equivalent methods under the term vacuum formed films (VFF). Since both melt, form, and recrystallize in a three dimensional shape, each of the processes may be used to form films wherein the loft of the cells are robust. Polymer webs have a property known as "memory" wherein a polymer web will tend to revert to its original shape. Therefore, if a polymer web is formed as a flat web and then forced into a three dimensional shape without undergoing melting and recrystallizing, the polymer web will try to revert again to its original flat shape when any stresses are subsequently applied. Robustness in the third dimension is critical for obtaining and then maintaining "loft", which prevents rewet.

Two important variables are commonly discussed when describing a VFF, loft and % AO. "Loft" is defined as the top to bottom thickness of the vacuum formed film, which is typically the required spacial distance between a fluid containing absorbent core and the skin of the user or the thickness of the vacuum formed film. Loft is typically measured by the same means used to measure "Embossed Thickness" in the polymer film industry. Embossment is merely imparting a third dimension to the film, typically ne with defined pattern and shape. Commonly used devices for this measurement are called "Low Load Micrometers". A wide area of displacement with a low compression load is utilized to insure one is measuring the full depth of pattern and one is not compressing the pattern to render a false reading. A TMI® Model 49-70 manufactured by Testing Machines, Inc. of Amityville, N.Y. was used for the loft measurements herein. This relationship of properties ties directly to rewet performance and is a simple calculation of dividing loft, as measured in microns ($\mu$), by the percent open area (17.3%, for example). As an example, a packing of 60 mesh round holes on a square pattern packing array, has a percent open area (OA %) that can be calculated as follows:

OA %={1 inch÷[mesh×mesh (due to square array)]×area of each hole, in inches}×100

A 60 mesh hole is 200$\mu$ in diameter, 200$\mu$/25.4 $\mu$/mil=7.8 mil or 0.0078 inch diameter, D/2=Radius; hence, Radius (R)=0.0039"

Area=$\pi R^2$=0.0039$^2$×3.14159=4.8×10$^{-5}$ mesh L×mesh=60×60=3600

{1÷[(4.8×10$^{-5}$)×3600]}×100=17.3% Open Area

For this invention it has been surprisingly discovered that by a combination of pattern, plane and texture, a VFF providing adequate "loft to % open area ratio" for achieving good rewet values can also attain a desirable silky tactile impression (STI).

Figure 1:
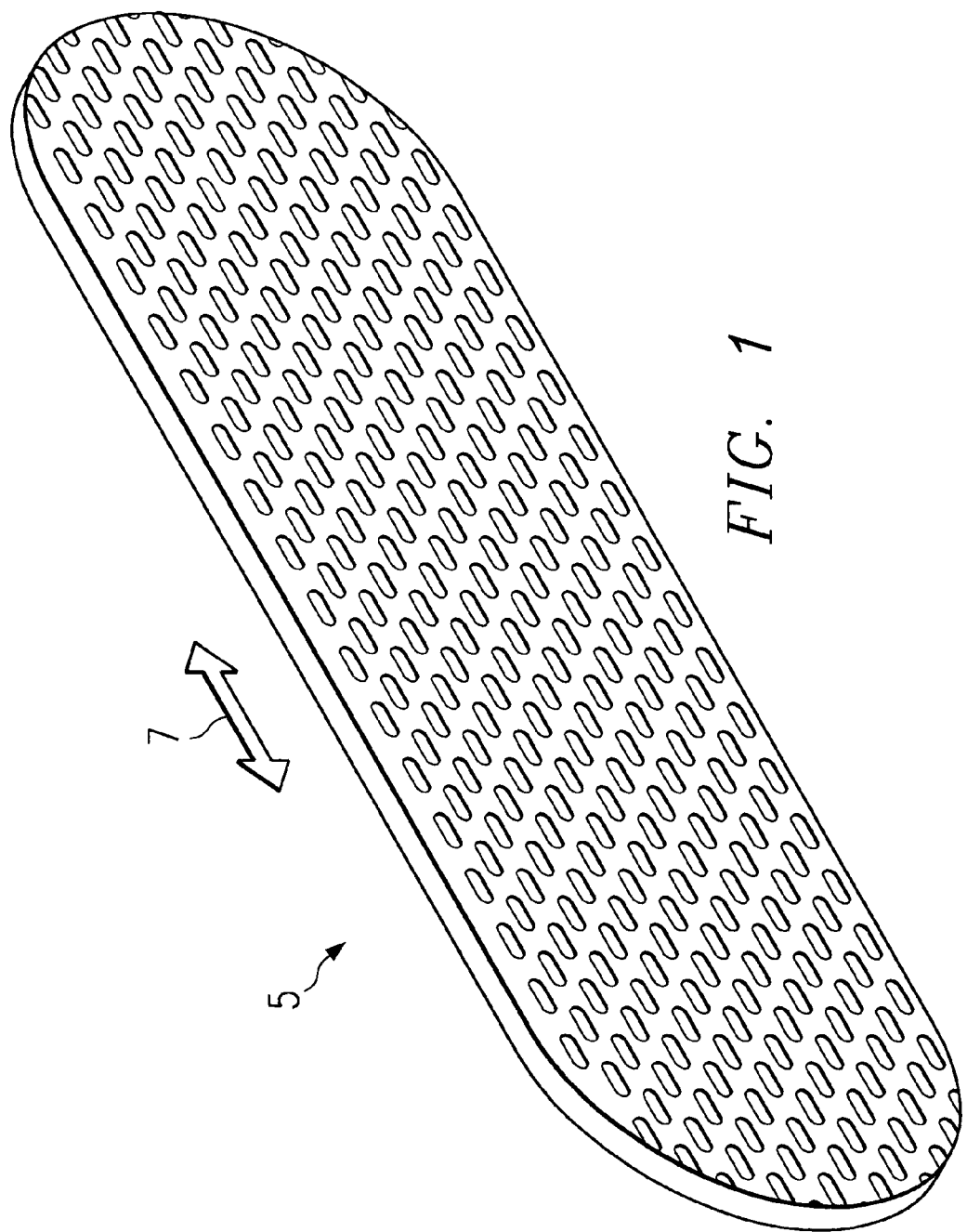
FIG. 1 is a perspective view of a feminine napkin utilizing a film of the invention.

It has been discovered that STI may be improved by selecting a specific range of mesh count from about 28 to 60, preferably 40. If fewer cells exist, it has been found that users can begin to sense the individuality of cells, which can detract from the STI effect. The STI may be further improved with an oval, boat shaped or elliptical cell having a major axis to minor axis ratio of at least about 1.05:1.0 to as much as about 6.5:1, more preferably ranging from about 1.5:1 to 4:1. The STI may be still further improved by aligning all the major axes substantially in the same direction. For purposes of this application, the stroking direction (SD) shall be defined as the direction along a length of an end product, e.g., feminine napkin or the like. FIG. 1 shows sample product 5. Arrow 7 shows the stroking direction. The stroking direction is typically the direction that a consumer strokes the material when assessing the film. It is desirable to align the stroking direction in a direction most likely to rub back and forth against a user during use, i.e. typically in a front to back orientation. By implementing the above steps, a discernable panel test result may be achieved for STI as compared to other VFF topsheets and synthetic silk-like nonwoven materials previously known in the art.

Further, it is commonly understood by those skilled in the art that the "machine direction" (MD) is the processing direction when manufacturing formed films, and with rare exception, when converting the formed film as a topsheet on an absorptive device. The MD is the direction where the web of the material(s) moves continuously down a machine. As it relates to the forming screens, the MD is the circumference of the screen and the "Transverse Direction" (TD) is from the end to end length of the screen. As is commonly understood, the forming screen rotates around a stationary seal. Therefore, the circumferential direction is the direction of continuous motion feeding film down the machine in the "Machine Direction". While not typical or commonly used, alterations from this norm will be understood by a man of the art; therefore, these are not intended as limiting to this invention.

On most conversion lines that take the VFF and place it as a topsheet, diapers or pads or bandages or whatever absorptive device is being manufactured will align the MD of topsheet down the length, or greatest dimension, of the product. Especially for feminine napkins, the difference of length to width is significant. In many tests when napkins are handed to women, they will typically stroke the topsheet down the length of the product as shown in FIG. 1. Consequently, it is generally the case that the stroking direction is synonymous with the machine direction, although this need not be the case to fall within the scope of the applicant's invention. For a consumer, the first perceptive triggers are gained by stroking the topsheet in the fashion described above when a consumer desires to know how the product will feel in use.

The length is also aligned with the anatomy of common disposable articles. Since disposable articles are typically held in the groin between the legs there is little chance of side to side or TD motion. If the product shifts during the natural motions of the user, the shift will almost always occur in the MD creating a "stroking" action of the topsheet against the skin. As explained above, and from all these correlated factors it can be seen that the term "MD" and "SD" are typically synonymous. The STI effect is gained by a stroking motion. Hence, the reference to the "Stroking Direction" (SD).

For purposes of this application, the term "oval" shall relate to a rounded shape with a major and minor axis whose lines along the major axis direction are essentially curved. The term "ellipse" shall differ in that the lines along the major axis direction are essentially straight. Hereafter, the ratio of major axes to minor axes shall be referred to as the SD:TD ratio wherein SD is the stroking direction's alignment of the major axes, and TD is the transverse direction of the minor axes. Although not essential for achieving the STI effect, it has been found that the STI effect is enhanced if the centers of major axes are commonly aligned with each other.

Again, while not essential for attaining STI effect, the STI effect may be further enhanced if the lands in the SD are on a slightly higher plane than the lands in the TD. Also, the STI can be triggered with this step alone. If SD lands are in a slightly higher plane, higher STI rankings are received when compared to single plane material of the same configuration. It has been found that as little as 15μ variance shows a slight distinction, although a 35μ variance is preferred. If a film has greater than a 145μ variance between the SD lands and the TD lands, then problems can occur with the strength of the forming screen, especially in the case of finer mesh counts. Winding issues, such as roll blocking due to nesting, may be introduced, as well. Since the SD lands are raised, it is less critical to have rounded cell geometries. Many polygonal shapes will also function, such as squares, hexagons, pentagons or other shapes.

The variance in the height of the planes of the SD land plane and the TD land plane can be achieved by machining a forming screen with cutting tools, grinding, etching, cutting with energy beams, or affixing wires to alter the external profile of the screen to form bi-planar lands. Additionally, other means may be used for varying the height of SD lands.

Also non-essential, but preferred, for increasing the STI effect is the addition of various texturizations to the lands. More preferred is the addition of micro-ridges (MR) of a specific height and spacing. Films having micro-ridges received surprisingly high panel test recognition of STI when the micro-ridges were applied to films having mesh counts of 28 or greater and especially to films having a 40 Hex pattern. To form micro-ridge patterns, the pattern is typically etched into the land areas of the screen. The micro-ridges will readily form on the lands of the film, so long as there remains a direct pathway of air evacuation in the spaces between the ridges. The air evacuation requirement applies to all patterns intended for texturization of the lands of the film. If the molten film lays over a cavity and forms a seal around a perimeter of the cavity, thereby sealing off an air evacuation pathway, the film will be prevented from being suctioned into micro-pattern depressions. Consequently, the film will be prevented from conforming to the shape of the micro-pattern depressions.

All or some of these features and enhancements, e.g, commonly aligned centers of major axes, elevated SD lands, and micro-ridges, may be combined to create a VFF material that will exhibit an STI effect among a majority of panelists assembled to test product. Other important aspects are maintaining the adequate VFF aperture diameter and product quality for transmission of fluids through the topsheet and into the absorbent core (especially the more viscous menses fluid), as well as maintaining the desired "loft to % open area ratio" of the VFF such that good rewet values are achievable.

Additionally, it has been shown that a preferred range of mesh count can contribute to the desired STI. As stated above, mesh count is the number of cells aligned in an inch of length. The higher the mesh count, the greater the number of cells that are packed together. The lower the mesh count, the fewer the number of cells in a given linear measure and/or square area. Cells or three-dimensional apertures may be patterned in any of a variety of arrays that are conducive to the desired objectives. Once an array is chosen, cells can then be counted per an inch of length to determine "mesh".

Figure 1A:
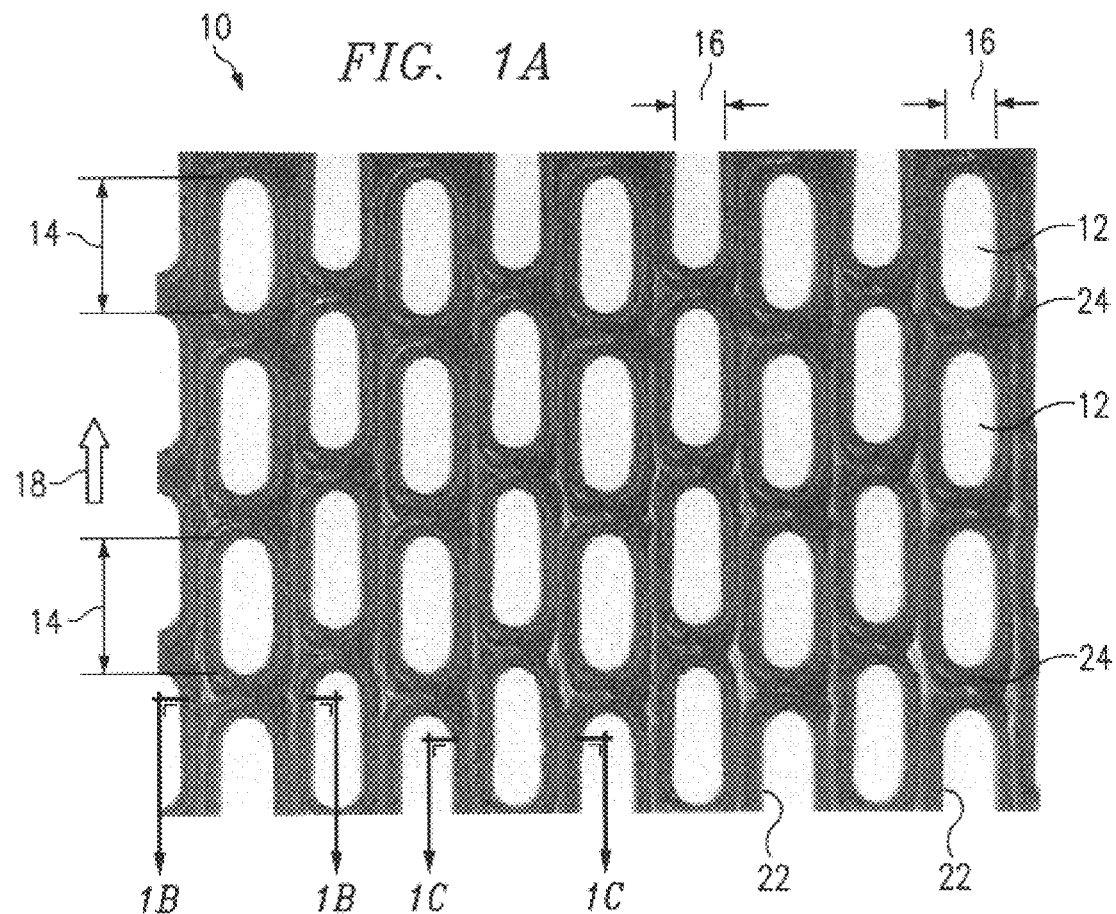
FIG. 1A is an plan view of a section of forming screen having an oriented ellipse pattern.

Referring now to FIG. 1A, a section of forming screen 10, which exhibits an oriented ellipse-pattern is shown. In the preferred pattern, ellipse shaped cells or apertures 12 have a major axis 14 and a minor axis 16. The major axis 14 is aligned in the machine direction (MD), which is indicated by arrow 18. The transverse direction (TD), is indicated by arrow 20. In a preferred embodiment, the ratio of lengths of major axis 14 to minor axis 16, i.e., "SD:TD" is about 3:1. Preferably, all major axes 14 are aligned with each other and are aligned in the machine direction 18. Additionally, all minor axes 16 are correspondingly aligned in the TD 20. Areas between cells 12 are SD lands 22 and TD lands 24.

Figure 1B:
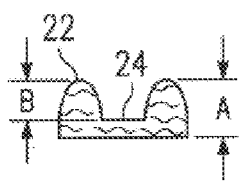
FIG. 1B is a cross-sectional view of the forming screen of FIG. 1A taken along line 1B—1B of FIG. 1A.
Figure 1C:
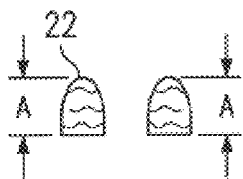
FIG. 1C is a cross-sectional view of the forming screen of FIG. 1A taken along line 1C—1C of FIG. 1A.

Referring now to FIG. 1B, a cross-section of forming screen 10 is shown taken along line 2—2 of FIG. 1A. FIG. 1B is an embodiment of forming screen 10 wherein SD land 22 is on a higher plane than TD land 24. The SD lands may be seen more clearly in FIG. 1C, which is a cross section of forming screen 10 taken along lines 1C—1C of FIG. 1A.

Figure 2A:
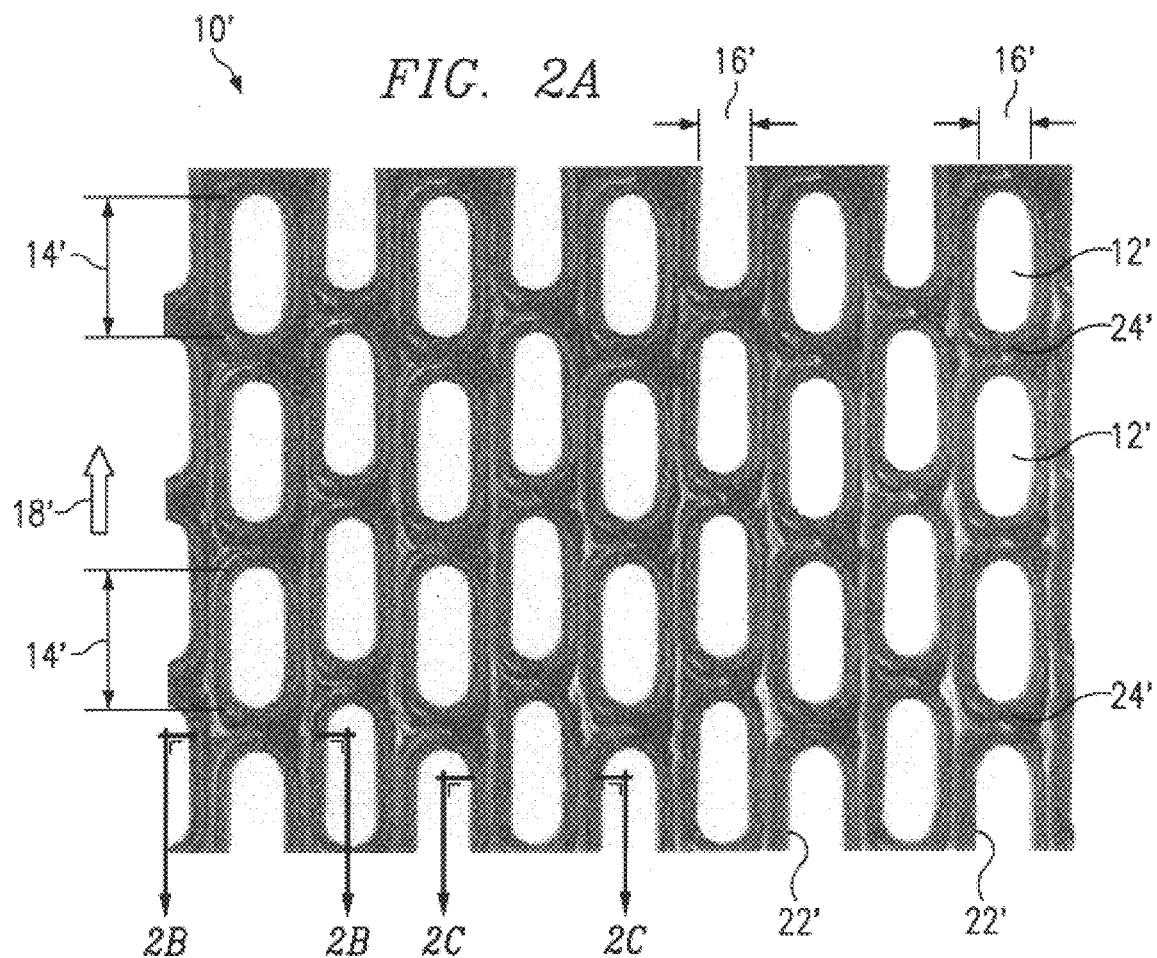
FIG. 2A is a plan view of a second embodiment of a section of forming screen having an oriented ellipse pattern.

Referring now to FIG. 2A, a section of forming screen 10', which exhibits an oriented ellipse pattern is shown. In the preferred pattern, ellipse shaped cells or apertures 12' have a major axis 14' and a minor axis 16'. The major axis 14' is aligned in the machine direction (MD), which is indicated by arrow 18. The transverse direction (TD), is indicated by arrow 20. In a preferred embodiment, the ratio of lengths of major axis 14' to minor axis 16', i.e., "SD:TD" is about 3:1. Preferably, all major axes 14' are aligned with each other and are aligned in the machine direction 18. Additionally, all minor axes 16' are correspondingly aligned in the TD 20. Areas between cells 12 are SD lands 22 and TD lands 24.

Figure 2B:
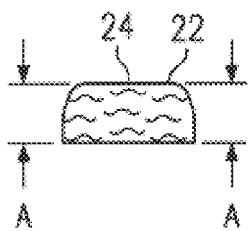
FIG. 2B is a cross-sectional view of the forming screen of FIG. 2A taken along line 2B—2B of FIG. 2A.
Figure 2C:
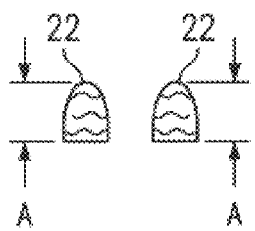
FIG. 2C is a cross-sectional view of the forming screen of FIG. 2A taken along line 2C—2C of FIG. 2A.

Referring now to FIG. 2B, a cross-section of forming screen 10' taken along lines 2B—2B is shown. FIG. 2B depicts an embodiment wherein an upper surface of SD land 22' and TD land 24' are in the same plane. The SD lands may be seen more clearly in FIG. 2C, which is a cross-section of forming screen 10' taken along lines 2C—2C of FIG. 2B.

Figure 3:
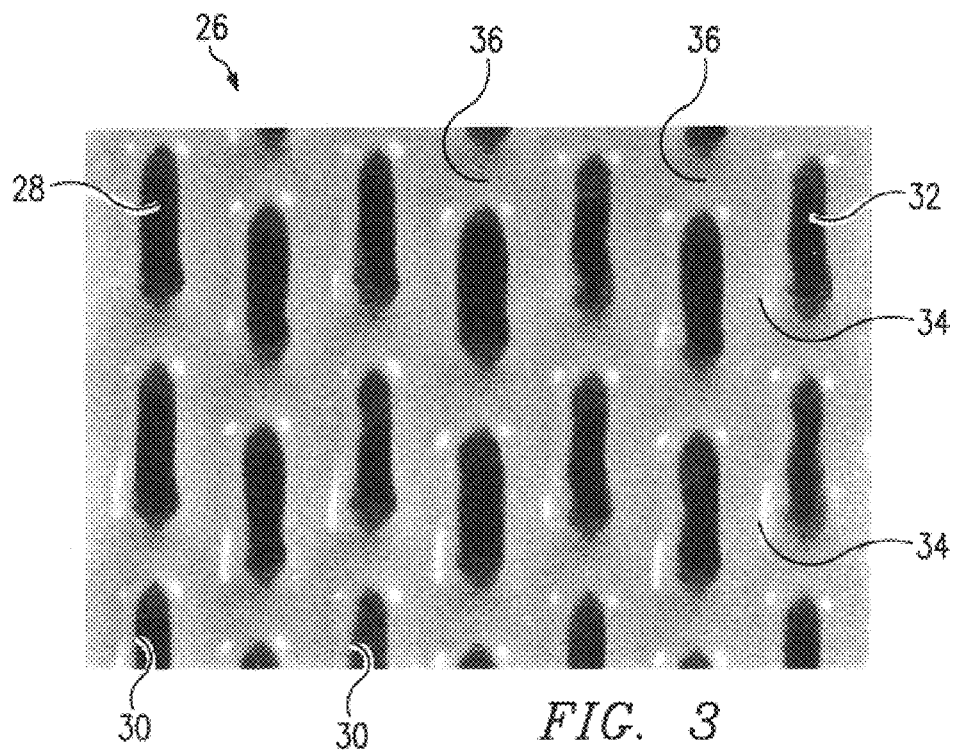
FIG. 3 is a plan view of a section of film having an oriented ellipse pattern wherein the film has a single plane on all lands.

Referring now to FIG. 3, a single plane VFF 26 is shown. VFF 26 is produced from a forming screen having an elliptical pattern with MD alignment of the major axes 28 of cells 30. The pattern shown in FIG. 26 is a 40 mesh pattern when counting cells in the TD. Apertures 30 of vacuum formed film 26 measures about 750μ in the SD or major axis 28 direction and about 250μ in the TD or minor axis 32 direction. The thickness of the cells, which are from top to bottom of the three-dimensional cells 30, i.e, loft, is about 345μ. The VFF 26 has an open area of 14.5%. Therefore, the loft to % open area ratio of the VFF 26 is about 24. The VFF 26 has a rewet value of 0.08 grams. The variance between the upper surface of the SD lands 34 and the TD lands 36 in the bi-planar material 26 is about 20μ.

Figure 4:
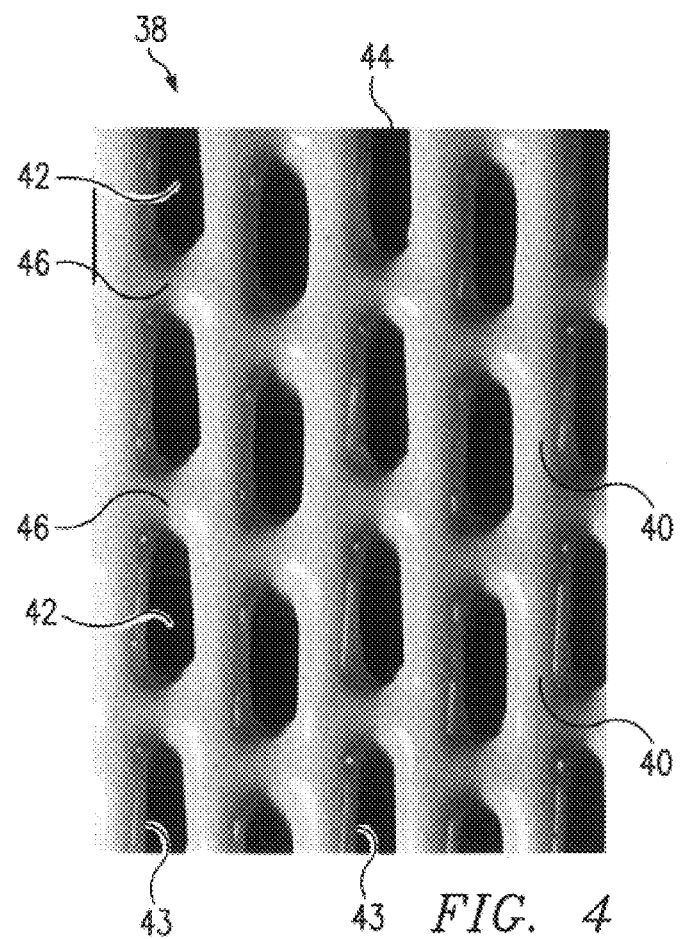
FIG. 4 is a plan view of a section of film having an oriented ellipse pattern wherein the film has a highest plane on stroking direction lands.

Referring now to FIG. 4, a multi-plane VFF 38 is shown wherein the highest plane is the upper surface of the SD lands 40. VFF 38 is produced from a forming screen having an elliptical pattern with MD alignment of the major axes 42 of cells 43. The pattern shown in FIG. 6 is a 40 mesh pattern. Cells 43 of vacuum formed film 38 measure about 750μ in the SD or major axis 42 direction and about 250μ in the TD or minor axis 44 direction. The thickness of the apertures 43, which are from top to bottom of the three-dimensional cells 43, i.e, loft, is about 345μ. The VFF 38 has an open area of 14.5%. Therefore, the loft to % open area ratio of the VFF 38 is about 24. The VFF 38 has a rewet value of 0.08 grams. The variance between the upper surface of the SD lands 40 and the TD lands 46 in the bi-planar material 38 is about 20μ.

Figure 5A:
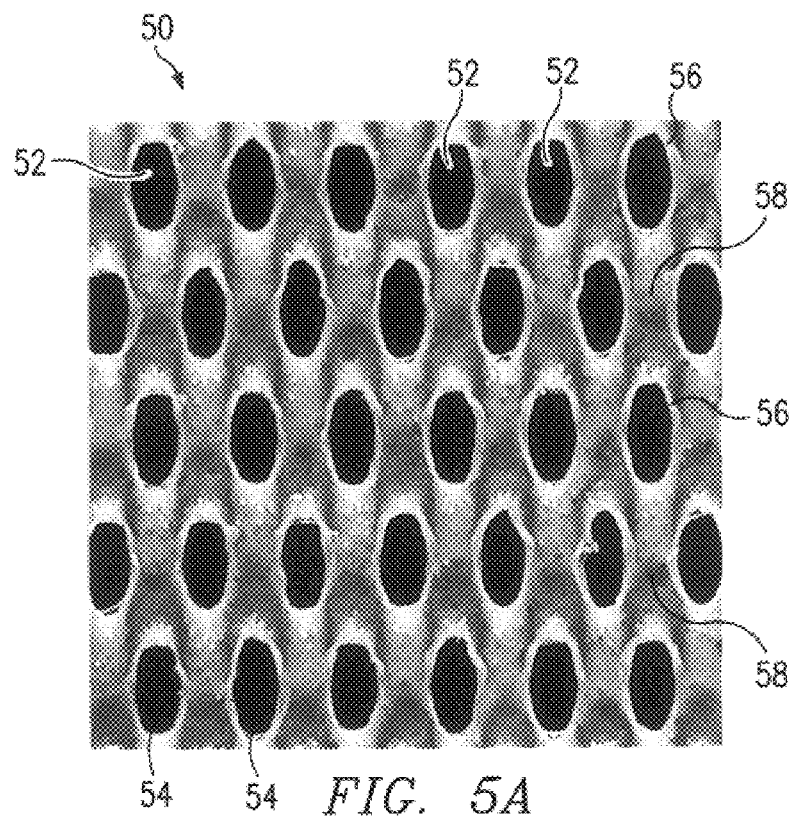
FIG. 5A is a plan view of a male side of a section of film having boat shaped cells.
Figure 5B:
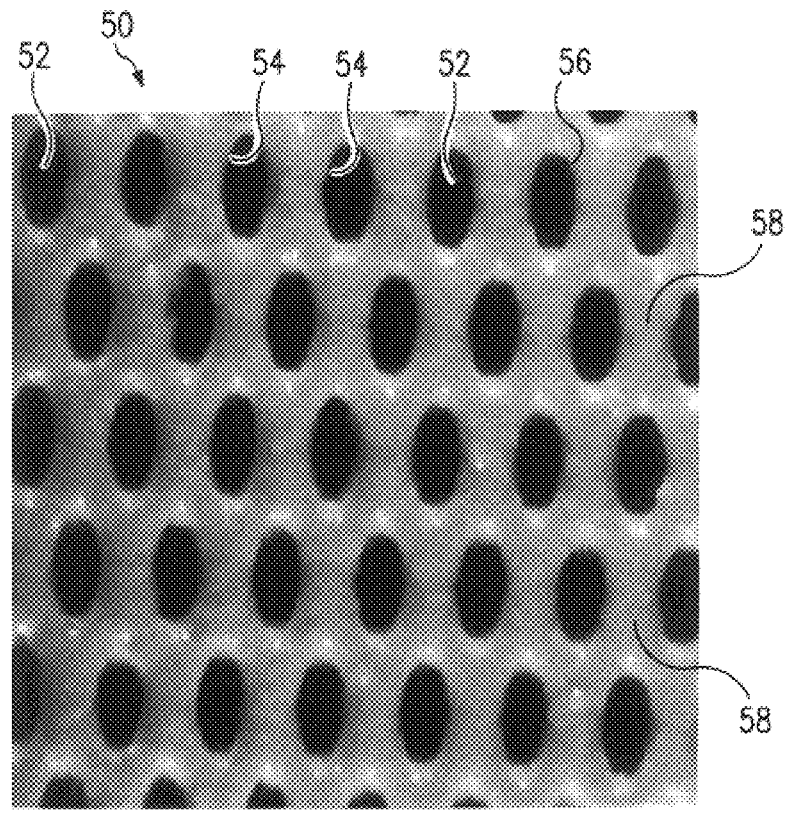
FIG. 5B is a plan view of a female side of a section of film having boat shaped cells.

Referring now to FIGS. 5A and 5B, FIGS. 5A and 5B show another embodiment of VFF that shall be referred to as a VFF having "Boat Shape Cells" (BSC) 50. The "Boat Shaped Cell" embodiment 50 preferably has a mesh count of 40. "Boat Shape Cell" refers to the oval shape apertures 52 having rounded tips. Apertures 52 have a major axis 54 and a minor axis 56. Preferably, the ratio of length of major axis 54 to minor axis 56 of the cells is about 1.75:1. It has been found that rounding off the extremities of either an oval shaped cell, as shown in FIGS. 5A and 5B, or an ellipse shaped cell, as shown in FIGS. 3 and 4, further enhances the STI, especially in a single plane material. The BSC embodiment 50 of FIGS. 5A and 5B has cells 50 having a length along the major axis 54 of about 425$\mu$ and a length along the minor axis of about 240$\mu$. The BSC film 50 has a loft of 315$\mu$ and an open area of 22%, which yields a loft to % open area ratio of 14 and a rewet value of 0.15 grams. Of course, the above dimensions are illustrative and other dimensions of may be used.

An additional feature of the BSC embodiment 50 is that the major axis 54 of the boat shaped cells or three dimensional apertures 52 are aligned in the SD but are not commonly aligned with each other, i.e., the cells 52 are presented in a "staggered" arrangement. Consequently, SD lands 58 are not straight as is the case with SD lands 34 (FIG. 3) and 40 (FIG. 4) of VFF films 26 and 38, respectively. A film having bi-planar lands, e.g, the embodiment shown in FIGS. 1A and 1B, are not preferred for the staggered BSC embodiment because it has been found that bi-planar lands are best achieved when all the SD lands, e.g. 34 and 40 are co-aligned with each other. Despite these less preferred variations, it has been found that panelists have still been able to derive a noticeable STI from the 40 mesh BSC (when counting the mesh in the TD) embodiment 50. Application of a random matte texture to the lands further enhances the material and slightly improves a panel's STI rating of the material.

Figure 6A:
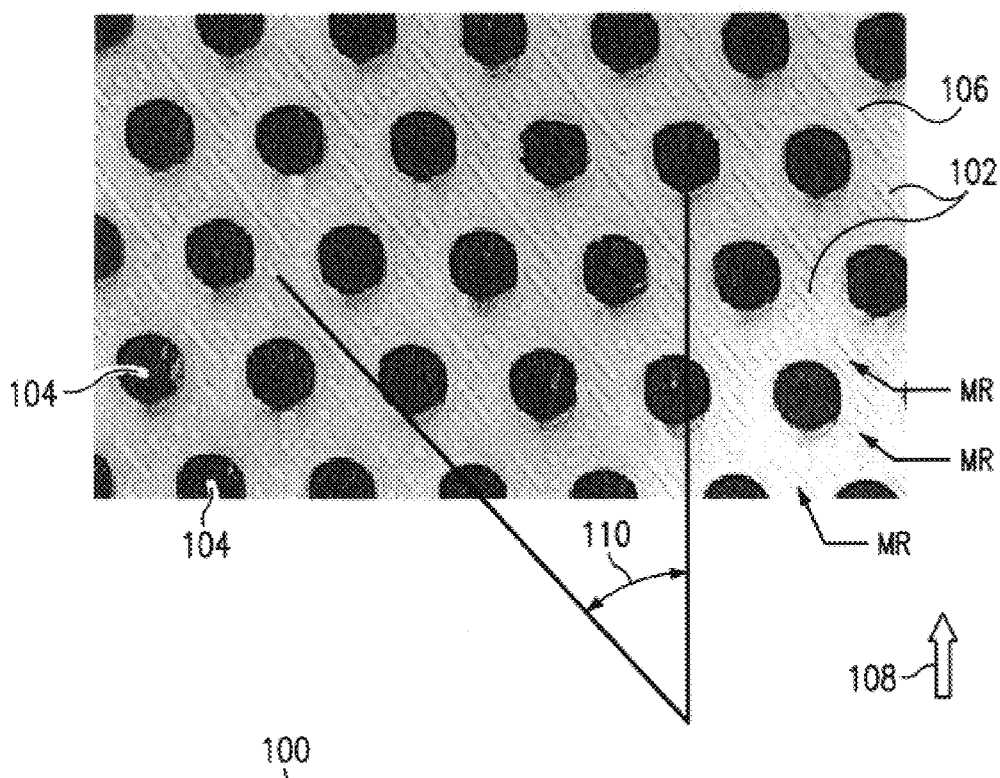
FIG. 6A is a plan view of a female side of a formed film material having micro-ridges on the lands of the film.
Figure 6B:
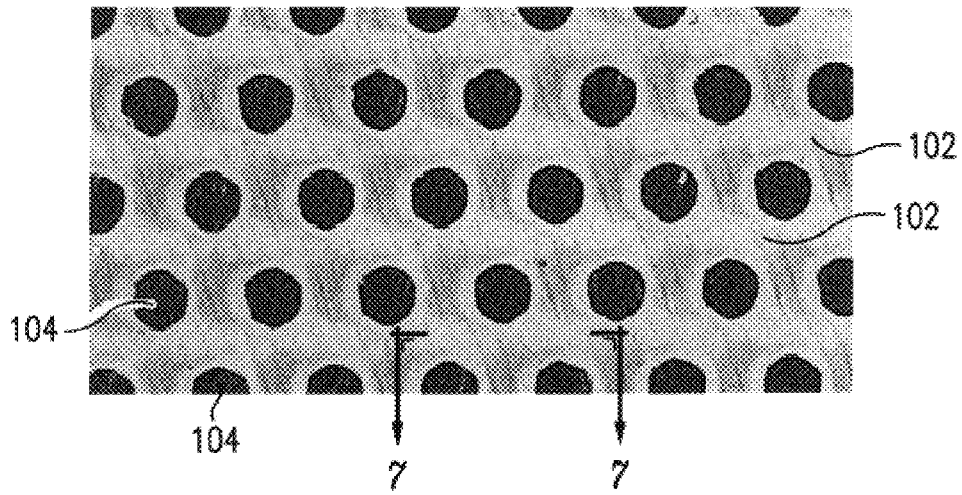
FIG. 6B is a plan view of a male side of a formed film material having micro-ridges on the lands of the film.
Figure 7:
FIG. 7 is a cross-sectional view of the formed film material of FIGS. 6A and 6B taken along line 7—7 of FIG. 6B.

While it is known that the addition of any of the aforementioned VFF-capable textures to the lands will contribute to improvement of the tactile impression and eliminate any perceptive triggers that are indicative of a plastic type material, it has surprisingly been found that "micro-ridges" (MR) alone can create a perceptible STI. Referring to FIGS. 6A, 6B and 7, microphotographs of a top view of VFF 100 (the side to the user; FIG. 6A) and a bottom view of VF 100 (the side away from the user; FIG. 6B), and an expanded graphic in cross-section of VFF 100 (FIG. 7) are given to show the MR of this invention. VFF 100 has a 40 hex pattern. To form textures on lands 102 of VFF 100, lands on a forming screen that is used to make VFF 100 are ground to be substantially flat to accept the artwork for etching the micro-ridges in the land region of the forming screen. As a result, lands 102, formed between apertures 104, are imparted with micro-ridges 106. The machine direction (MD) or stroking direction (SD) is indicated by arrow 108.

Micro-ridges 106 preferably have individual distinction with a range of height and spacing and have an optimum STI effect when aligned on a bias, i.e., at offset angle 110 to the SD 108. Offset angle 110 may be 5° to 80° to achieve some effect, but the preferred range for offset angle 110 is from 30° to 60°, and ideally 45° is used. The height of the MR 106 can range from 5$\mu$ to 75$\mu$, but the preferred range is from 5$\mu$ to 35$\mu$. Ideally, MR 106 have a height of 20$\mu$. Spacing between micro-ridges 106 can range from 25$\mu$ to 250$\mu$, but more preferably range from 50$\mu$ to 150$\mu$. Most preferably, a 95$\mu$ spacing is used. The micro-ridges 106 must also maintain "individuality". If micro-ridges 106 become interconnected, then micro-ridges 106 will not create the desired STI but rather the micro-ridges 106 will exhibit a planar and plastic-like feel instead.

As used herein, the symbols "$\mu$" and "$\mu$m" are synonymous, and both mean micrometer.

TEST DATA

Various formed films were tested by ten panelists for silky tactile impression (STI). The results are presented in Table 2, below. The panel method was based upon the AATCC (1997) Evaluation Procedure 5, Fabric Hand: Guidelines for the Subjective Evaluation of Fabric, a Technical Manual of the American Association of Textile Chemists and Colorists, Volume 72 (pp.352–354), Research Triangle Park, NC; and, ASTM (1968) Manual on Sensory Testing Methods, ASTM Special Technical Bulletin 434, 1968, pp.3–5.

The evaluation procedure utilized a common pad of standard thickness and material yielding a standard compressibility. Values for thickness and compressibility are not particularly important, so long as the values are consistent. The pad was cut into 1.5"×3.0" rectangles. The films were wrapped fully around and taped closed, much like wrapping a gift, leaving on one side a continuous, smooth area of material. The continuous, smooth side comprise the tested side. Panelists washed their hands so that the samples were not tainted; tainting potentially creating an anomalous variance between panelist one and panelist ten, as the samples are passed from one panelist to another.

The samples were coded by an identifier, such as a number or letter, but no information was provided to avoid any pre-biasing of a panelist. The panelists were asked to rate the samples from 1 to 10 with 1 being the silkiest and 10 being not silky.

All but one of the products in the test data of Table 2 below are apertured film embodiments, except for "Unicharm's TS Threads on NW". The Unicharm product is not a formed film product, but it has been added to Table 2 because it is recognized as succeeding as a feminine napkin topsheet in Asia and is known to be viewed as triggering a favorable STI. It is constructed by an unknown method wherein synthetic silk threads are bonded to a top plane (skin contact side) of a nonwoven web. Holes are punched through the material, apparently to increase the rate of fluid acquisition. Its fluid acquisition rate value is believed to be over 3.0 grams. The Unicharm product is included here to assist in obtaining a stronger reading on the panel test's apparent line of separation between STI and non-STI materials. Also included for that purpose is Comfort Silk®.

Comfort Silk® is a mechanically formed apertured film but is not a VFF. It too has been accepted as "Silky" in the marketplace. Therefore, the inclusion of Comfort Silk® aids in making STI and non-STI distinctions.

In reviewing the data, it is commonly accepted that an average ranking of a film by ten panelists of a value of ≦5.0 indicates a STI is discernable. The number of No. 1 rankings given by panelists can also serve as an indication that an STI has been 'triggered'.

TABLE 2

| Testers | MD Ellipse | 40 Hex FlatLand w/Micro Ridges | 40 BSC | Unicharm's TS Threads on NW | Comfortsilk | Always | Equate |
|---|---|---|---|---|---|---|---|
| 1 | 6 | 3 | 2 | 5 | 1 | 8 | 10 |
| 2 | 4 | 1 | 3 | 7 | 2 | 10 | 6 |
| 3 | 1 | 2 | 4 | 5 | 3 | 9 | 10 |
| 4 | 2 | 1 | 6 | 3 | 5 | 8 | 10 |
| 5 | 3 | 1 | 6 | 4 | 5 | 10 | 8 |
| 6 | 5 | 1 | 3 | 6 | 2 | 9 | 7 |
| 7 | 1 | 4 | 7 | 6 | 3 | 5 | 10 |
| 8 | 2 | 1 | 6 | 4 | 5 | 8 | 10 |
| 9 | 6 | 1 | 5 | 4 | 2 | 10 | 8 |
| 10 | 5 | 3 | 1 | 6 | 2 | 9 | 10 |
| AVG. | 3.5 | 1.8 | 4.3 | 5 | 3 | 8.6 | 8.9 |

Rate the samples from 1 to 10 for Silkiness Testing.
1 = "Silkiest": 10 = "not Silky"

Another important test for comparing various films is a "Rewet Test". For testing rewet a test fluid comprising two parts Pepto-Bismol® and one part distilled water was used. The sample assembly consisted of a 5×5 inch piece of vacuum formed film or nonwoven topsheet placed with the user side up and the garment side down over 3 plies of absorbent medium. An amount of 2-ml test fluid was delivered through a pipette onto the center surface of the topsheet. The time, in seconds, taken for all of the liquid to penetrate through the topsheet was recorded with a stopwatch. This portion of the test indicates the fluid acquisition rate. After the initial insult, an additional 15-ml of the test fluid was delivered to the center surface of the topsheet. An 8 lbs rewet weight with a 4×4 inch footing was placed on the top of the topsheet for 3 minutes for the fluid to thoroughly spread out into the core pads. Then, two pre-weighted pickup papers were pressed against the topsheet with the 8 lbs rewet weight for an additional 2 minutes. The amount of weight increase of the pickup papers was measured in grams as the rewet amount, which reflects the amount of fluid that successfully reversed flow and overcame the spatial separation of the topsheet material. It has been found that data using this fluid for both acquisition rate and rewet values correlates well to comparative data generated from the same VFF materials tested by this method and by undisclosed methods used by major corporations who produce feminine napkin products.

Table 3, below, compares existing products and shows that embodiments of this invention provide a desirable STI, and also maintain a L/OA Ratio that exhibits functional rewet:

TABLE 3

| Product | Loft, $\mu$ | Open Area, % | L/OA Ratio | Rewet, grams | STI (Y/N) |
|---|---|---|---|---|---|
| Always | 550 | 32.0 | 17.0 | 0.05 | N |
| Equate | 455 | 28.5 | 16.0 | 0.15 | N |
| ComfortSilk | 115 | 28.5 | 4.0 | 1.25 | Y |
| SD Ellipse 38 | 345 | 14.5 | 23.8 | 0.08 | Y |
| 40 Mesh BSC 50 | 315 | 22.0 | 14.3 | 0.15 | Y |

It is thus believed that the operation and construction of the present invention will be apparent from the foregoing description. While the apparatus and compositions shown or described have been characterized as being preferred it will be obvious that various changes and modifications may be made therein without departing from the spirit and scope of the invention as defined in the following claims.

I claim:

1. A vacuum formed film for use in a disposable absorbent article, the film comprising:
    a three dimensional film containing a plurality of cells defining lands in areas between said cells;
    microridges on said lands having a center to center spacing of about 50 $\mu$m to about 150 $\mu$m and a height of about 5 $\mu$m to about 75 $\mu$m, said microridges having a length and a width;
    a plurality of said microridges each having its length substantially greater than its width, and said plurality of microridges being substantially parallel along their lengths.
2. The film of claim 1 wherein:
    the film has a Silky Tactile Impression Rating of less than 4.
3. The film of claim 1 wherein:
    the film has a loft to open area ratio of greater than 9.
4. The film of claim 1 wherein:
    the film has a rewet of less than 1 gram.
5. The film of claim 1 wherein:
    said plurality of microridges are offset from the machine direction at an angle between 5° and 80°.
6. The film of claim 1 wherein:
    each of said plurality of microridges are separate and discontinuous from each other of said plurality of microridges.
7. The film of claim 1 wherein:
    the film is a direct melt vacuum formed film.
8. A vacuum formed film for use in a disposable absorbent article, the film comprising:
    a three dimensional film containing a plurality of cells defining lands in areas between said cells;
    microridges on said lands having a height of about 5 $\mu$m to about 75 $\mu$m, said microridges having a length and a width;
    a plurality of said microridges each having its length substantially greater than its width; and
    the film having a Silky Tactile Impression Rating of less than 5.
9. The film of claim 8 wherein:
    said plurality of microridges are substantially parallel along their lengths and are offset from the machine direction at an angle between 5° and 80°.

* * * * *

UNITED STATES PATENT AND TRADEMARK OFFICE
CERTIFICATE OF CORRECTION

PATENT NO. : 6,582,798 B2
DATED : June 24, 2003
INVENTOR(S) : Paul E. Thomas

It is certified that error appears in the above-identified patent and that said Letters Patent is hereby corrected as shown below:

Column 1,
Line 66, replace "pattens" with -- patterns --

Column 3,
Line 2, replace "$\geqq$" with -- $\geq$ --

Column 4,
Line 49, replace "an" with -- a --

Column 5,
Line 37, replace "ne" with -- one --

Column 9,
Line 16, delete "of"

Column 10,
Line 64, replace "$\leqq$" with -- $\leq$ --

Signed and Sealed this

Second Day of December, 2003

JAMES E. ROGAN
*Director of the United States Patent and Trademark Office*